(12) United States Patent
Kaizaki

(10) Patent No.: US 7,943,793 B2
(45) Date of Patent: May 17, 2011

(54) OPTICALLY ACTIVE ORGANIC ACIDATE-BRIDGED DINUCLEAR PLATINUM(II) COMPLEX

(75) Inventor: Sumio Kaizaki, Suita (JP)

(73) Assignee: Osaka University, Osaka (JP)

( * ) Notice: Subject to any disclaimer, the term of this patent is extended or adjusted under 35 U.S.C. 154(b) by 10 days.

(21) Appl. No.: 12/450,470

(22) PCT Filed: Mar. 27, 2008

(86) PCT No.: PCT/JP2008/055942
§ 371 (c)(1),
(2), (4) Date: Dec. 29, 2008

(87) PCT Pub. No.: WO2008/120690
PCT Pub. Date: Oct. 9, 2008

(65) Prior Publication Data
US 2010/0121090 A1 May 13, 2010

(30) Foreign Application Priority Data
Mar. 29, 2007 (JP) .................. 2007-087124

(51) Int. Cl.
*C07F 15/00* (2006.01)
*A61K 31/28* (2006.01)
(52) U.S. Cl. ........................ 556/137; 514/492
(58) Field of Classification Search ........... 556/137; 514/492
See application file for complete search history.

(56) References Cited

OTHER PUBLICATIONS

English Translation of the International Preliminary Report on Patentability.
Y. Igawa et al., "Synthesis of Novel L-Tartrate-Bridged Dinuclear Copper(II) Complexes and Their Properties", The 53$^{rd}$ Symposium, Japan Society of Coordination Chemistry, Abstracts, p. 11 (1Aa01), Sep. 10, 2003 along with its English translation.

*Primary Examiner* — Porfirio Nazario Gonzalez

(74) *Attorney, Agent, or Firm* — Wenderoth, Lind & Ponack, L.L.P.

(57) ABSTRACT

The present invention is an optically active organic acidate-bridged dinuclear platinum(II) complex represented by the general formula (I):

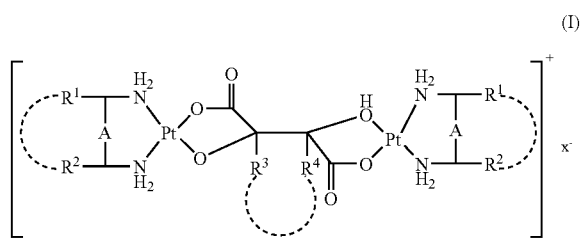

(I)

or the general formula (I'):

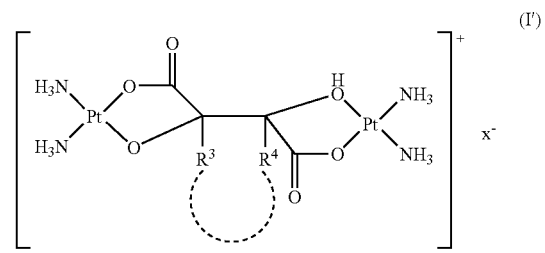

(I')

(wherein $R^1$ and $R^2$ are the same or different and each represent a hydrogen atom or an alkyl group, or form an alkylene group by binding to each other at the ends thereof;
$R^3$ and $R^4$ are the same or different and each represent a hydrogen atom or an alkyl group, or form an alkylene group by binding to each other at the ends thereof;
A represents a single bond or a methylene group; and
$X^-$ represents an anion).

The complex of the present invention has an excellent anticancer activity, and is useful as medicine, especially an anticancer agent.

10 Claims, No Drawings

OPTICALLY ACTIVE ORGANIC ACIDATE-BRIDGED DINUCLEAR PLATINUM(II) COMPLEX

This application is a U.S. national stage of international Application No. PCT/JP2008/055942 filed Mar. 27, 2008.

TECHNICAL FIELD

The present invention relates to an optically active organic acidate-bridged dinuclear platinum(II) complex with an excellent anticancer activity, a preparation method thereof, and use thereof.

BACKGROUND ART

Anticancer platinum complexes are known as one of anticancer agents, and cisplatin (chemical name: cis-diamminedichloridoplatinum(II)) was developed as the first anticancer platinum complex. However, there is a problem with cisplatin in that it has many side effects, such as nephrotoxicity, haematotoxicity, gastrointestinal toxicity and neurotoxicity. Then, carboplatin (chemical name: cis-diammine(1,1-cyclobutanedicarboxylato)platinum(II)) was next developed to reduce the nephrotoxicity of cisplatin and to increase its water solubility, but it does not necessarily have a satisfactory anticancer activity. Then, oxaliplatin (chemical name: oxalato(1R,2R-1,2-cyclohexanediamine)platinum(II)) was developed as the third generation of anticancer platinum complexes (the patent literature 1). Oxaliplatin has an anticancer activity even against cisplatin-resistant cancer cells and little toxicity such as nephrotoxicity and haematotoxicity, and therefore excels among others, but there is still room for improvement in respect of the anticancer activity.

Meanwhile, the intracellular target molecule of the aforementioned platinum complexes is DNA, and the platinum complexes are considered to exhibit an anticancer activity by forming cross-links with a constituent base of DNA. Examples of the cross-link formations include DNA-protein cross-links, DNA intrastrand cross-links and DNA interstrand cross-links. Cisplatin, for example, is considered to form DNA intrastrand cross-links and/or DNA interstrand cross-links.

DNA has a helical structure, which is a chiral structure. For this reason, when the platinum complexes bind to DNA, their chirality is anticipated to greatly affect their own anticancer activity, but at present, it is not clear how the chirality affects the anticancer activity.

Patent Literature 1: JP-A 6-211883

SUMMARY OF INVENTION

Problem to be Solved by the Invention

An object of the present invention is to provide a novel platinum complex which is superior in anticancer activity to oxaliplatin and highly selective in its action on cancer cells. Another object thereof is to provide a method for preparing the novel platinum complex. A further object thereof is to provide an anticancer agent comprising the novel platinum complex as an active ingredient.

Means for Solving the Problem

The present inventor conducted extensive research to develop such a novel platinum complex which is superior in anticancer activity to oxaliplatin and highly selective in its action on cancer cells. As a result, he successfully generated an unprecedented optically active organic acidate-bridged dinuclear platinum(II) complex, and found that the complex exhibits an excellent anticancer activity and that the activity is diastereoselective. He conducted further research based on the above findings, and finally completed the present invention.

Namely, the present invention relates to the following (1) to (10):

(1) an optically active organic acidate-bridged dinuclear (diamine)platinum(II) complex represented by the general formula (I):

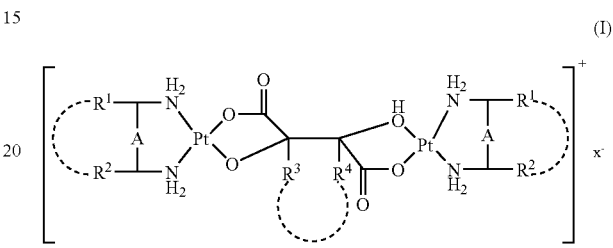

(I)

(wherein $R^1$ and $R^2$ are the same or different and each represent a hydrogen atom or an alkyl group, or form an alkylene group by binding to each other at the ends thereof;
$R^3$ and $R^4$ are the same or different and each represent a hydrogen atom or an alkyl group, or form an alkylene group by binding to each other at the ends thereof;
A represents a single bond or a methylene group; and
$X^-$ represents an anion), (2) the compound according to the above (1), wherein $R^1$ and $R^2$ form an alkylene group by binding to each other at the ends thereof and $R^3$ and $R^4$ are hydrogen atoms, (3) the compound according to the above (2), wherein the alkylene group which $R^1$ and $R^2$ form by binding to each other at the ends thereof is tetramethylene, (4) the compound according to any of the above (1) to (3), wherein A is a single bond, (5) the compound according to any of the above (1) to (4), wherein $X^-$ is a nitrate ion, (6) a method for preparing an optically active organic acidate-bridged dinuclear (diamine)platinum(II) complex represented by the general formula (I):

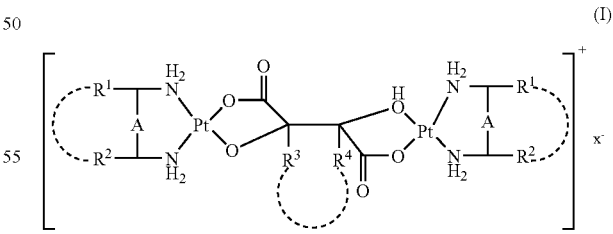

(I)

(wherein $R^1$ and $R^2$ are the same or different and each represent a hydrogen atom or an alkyl group, or form an alkylene group by binding to each other at the ends thereof;
$R^3$ and $R^4$ are the same or different and each represent a hydrogen atom or an alkyl group, or form an alkylene group by binding to each other at the ends thereof;
A represents a single bond or a methylene group; and
X represents an anion), which is characterized by reacting a platinum complex represented by the general formula (II):

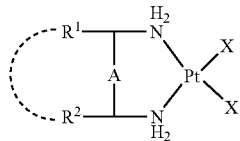
(II)

(wherein X represents an anion ligand, and the other symbols have the same meanings as above)
with an optically active organic acid represented by the general formula (III):

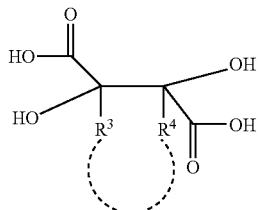
(III)

(wherein each symbol has the same meaning as above),
(7) an anticancer agent comprising, as an active ingredient, an optically active organic acidate-bridged dinuclear (diamine)platinum(II) complex represented by the general formula (I):

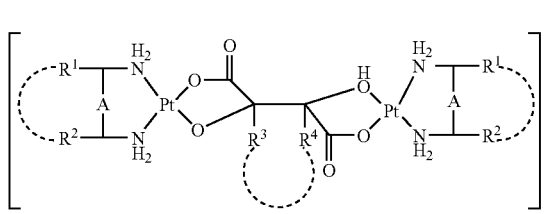
(I)

(wherein $R^1$ and $R^2$ are the same or different and each represent a hydrogen atom or an alkyl group, or form an alkylene group by binding to each other at the ends thereof;
$R^3$ and $R^4$ are the same or different and each represent a hydrogen atom or an alkyl group, or form an alkylene group by binding to each other at the ends thereof;
A represents a single bond or a methylene group; and
$X^-$ represents an anion),
(8) an optically active organic acidate-bridged dinuclear diammineplatinum(II) complex represented by the general formula (I'):

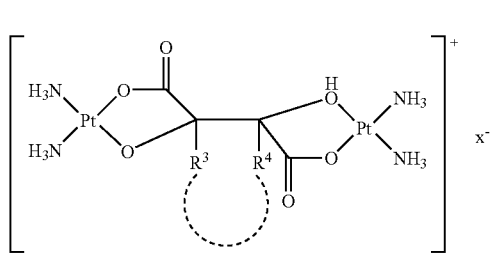
(I')

(wherein $R^3$ and $R^4$ are the same or different and each represent a hydrogen atom or an alkyl group, or form an alkylene group by binding to each other at the ends thereof; and $X^-$ represents an anion),
(9) a method for preparing an optically active organic acidate-bridged dinuclear diammineplatinum(II) complex represented by the general formula (I'):

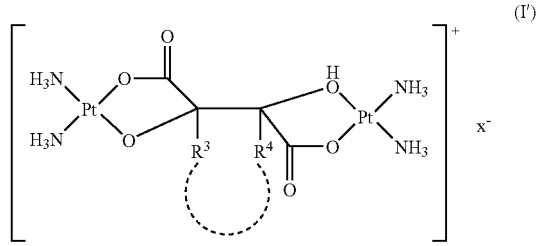
(I')

(wherein $R^3$ and $R^4$ are the same or different and each represent a hydrogen atom or an alkyl group, or form an alkylene group by binding to each other at the ends thereof; and $X^-$ represents an anion),
which is characterized by reacting a platinum complex represented by the general formula (II'):

(II')

(wherein X represents an anion ligand)
with an optically active organic acid represented by the general formula (III):

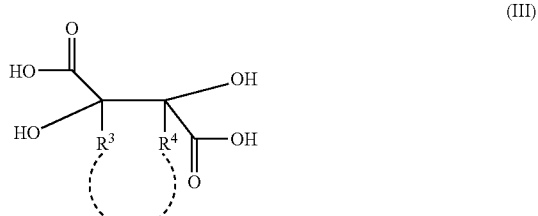
(III)

(wherein $R^3$ and $R^4$ have the same meanings as above), and
(10) an anticancer agent comprising, as an active ingredient, an optically active organic acidate-bridged dinuclear diammineplatinum(II) complex represented by the general formula (I'):

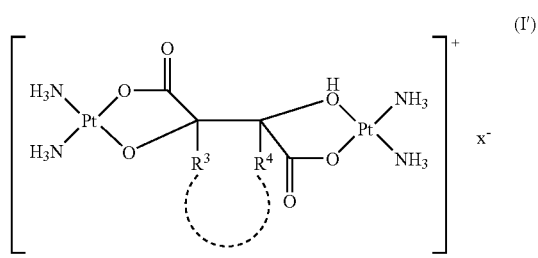
(I')

(wherein $R^3$ and $R^4$ are the same or different and each represent a hydrogen atom or an alkyl group, or form an alkylene group by binding to each other at the ends thereof; and $X^-$ represents an anion).

Effect of the Invention

The optically active organic acidate-bridged dinuclear platinum(II) complex of the present invention exhibits an excellent anticancer activity with diastereoselectivity.

BEST MODE FOR CARRYING OUT THE INVENTION

One embodiment of the present invention is an optically active organic acidate-bridged dinuclear (diamine)platinum(II) complex represented by the general formula (I):

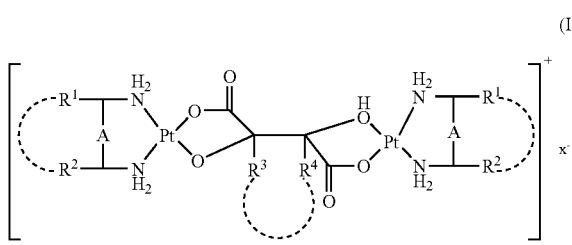

(I)

(wherein each symbol has the same meaning as above).
The complex consists of a positively charged platinum complex cation and a negatively charged anion ($X^-$). Because of different configurations of the respective chiral carbon atoms bound to $R^1$, $R^2$, $R^3$, and $R^4$, a plurality of diastereomers are present as the above complex and all the diastereomers are included in the present invention.

In the optically active organic acidate-bridged dinuclear (diamine)platinum(II) complex represented by the general formula (I), examples of the anion represented by $X^-$ include a nitrate ion ($NO_3^-$) and a chloride ion ($Cl^-$).

In the optically active organic acidate-bridged dinuclear (diamine)platinum(II) complex represented by the general formula (I), specifically, the symbols $R^1$ and $R^2$ are the same or different and are each a hydrogen atom or an alkyl group having 1 to 5 carbon atoms, or $R^1$ and $R^2$ form an alkylene group having 2 to 6 carbon atoms by binding to each other at the ends thereof. Inter alia, $R^1$ and $R^2$ preferably form tetramethylene by binding to each other at the ends thereof. Namely, this is the case where $R^1$ and $R^2$ together with the respective adjacent carbon atoms thereto form cyclohexanediamine.

In the optically active organic acidate-bridged dinuclear (diamine)platinum(II) complex represented by the general formula (I), specifically, the symbols $R^3$ and $R^4$ are the same or different and are each a hydrogen atom or an alkyl group having 1 to 5 carbon atoms, or $R^3$ and $R^4$ form an alkylene group having 2 to 5 carbon atoms by binding to each other at the ends thereof. Inter alia, it is preferable that $R^3$ and $R^4$ are each independently a hydrogen atom or an alkyl group having 1 to 5 carbon atoms. In the case where $R^3$ and $R^4$ are alkyl groups having 1 to 5 carbon atoms, or form an alkylene group having 2 to 5 carbon atoms by binding to each other at the ends thereof, the compound of the present invention is more lipophilic and easier to permeate the cell membrane, and therefore can be expected to have an enhanced anticancer effect.

Specific examples of the compound (I) of the present invention include nitrates and chlorides of the following compounds: L- or D-tartrate-bridged dinuclear 1R,2R-1,2-trans-cyclohexanediamine platinum(II) complex, L- or D-tartrate-bridged dinuclear ethylenediamine platinum(II) complex, L- or D-tartrate-bridged dinuclear R-1,2-propanediamine platinum(II) complex, L- or D-tartrate-bridged dinuclear 2R,3R-2,3-butanediamine platinum(II) complex, L- or D-tartrate-bridged dinuclear R,R-stilbenediamine platinum(II) complex, L- or D-tartrate-bridged dinuclear 1R,2R-1,2-trans-cyclopentanediamine platinum(II) complex, L- or D-tartrate-bridged dinuclear 1S,2R-2-(aminomethyl)cyclohexylamine platinum(II) complex, L- or D-tartrate-bridged dinuclear 2R,4R-2,4-pentanediamine platinum(II) complex, 1L,2L- or 1D,2D-2-methyltartrate-bridged dinuclear 1R,2R-1,2-cyclohexanediamine platinum(II) complex, 2L,3L- or 2D,3D-2,3-dimethyltartrate-bridged dinuclear 1R,2R-1,2-cyclohexanediamine platinum(II) complex, 1L,2L- or 1D,2D-1,2-dihydroxycyclopentane-1,2-dicarboxylate-bridged dinuclear 1R,2R-cyclohexanediamine platinum(II) complex, 1L,2L- or 1D,2D-1,2-dihydroxycyclohexane-1,2-dicarboxylate-bridged dinuclear 1R,2R-cyclohexanediamine platinum(II) complex, and their optical isomers (including diastereomers).

The compound (I) of the present invention can be prepared as follows, for example. Namely, the compound (I) can be prepared by reacting a compound represented by the general formula (II):

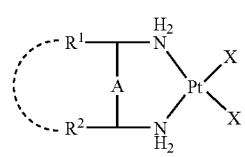

(II)

(wherein each symbol has the same meaning as above)
with an optically active organic acid represented by the general formula (III):

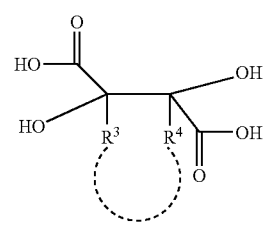

(III)

(wherein each symbol has the same meaning as above).

Specific examples of the compound (II), which is one of the starting materials for the above reaction, include dinitrato(diamine)platinum(II) complexes prepared in the following manner. A diamine compound represented by the general formula (IV):

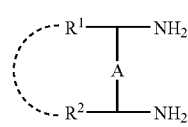

(IV)

is reacted with potassium tetrachloridoplatinate(II), and then with potassium iodide to give diiodido(diamine)platinum(II). Subsequently, the resulting compound is reacted with silver nitrate to give the objective compound.

Specific examples of the diamine compound (IV) include ethylenediamine (abbreviation: en); R- or S-1,2-propanediamine (abbreviation: R- or S-pn); 2R,3R- or 2S,3S-2,3-butanediamine (abbreviation: R,R- or S,S-bn); R,R- or S,S-stilbenediamine (abbreviation: R,R- or S,S-stien); 1R,2R- or 1S,2S-1,2-trans-cyclohexanediamine (abbreviation: R,R- or S,S-dach); 1R,2R- or 1S,2S-1,2-trans-cyclopentanediamine (abbreviation: R,R- or S,S-dacp); 1S,2S-, 1S,2R-, 1R,2S- or 1R,2R-2-(aminomethyl)cyclohexylamine (abbreviation: S,S-, S,R-, R,S- or R,R-amcha); and 2R,4R- or 2S,4S-2,4-pentanediamine (abbreviation: R,R- or S,S-ptn). Structural formulae of the above compounds are shown below (among a plurality of stereoisomers, a general example is represented in each case):

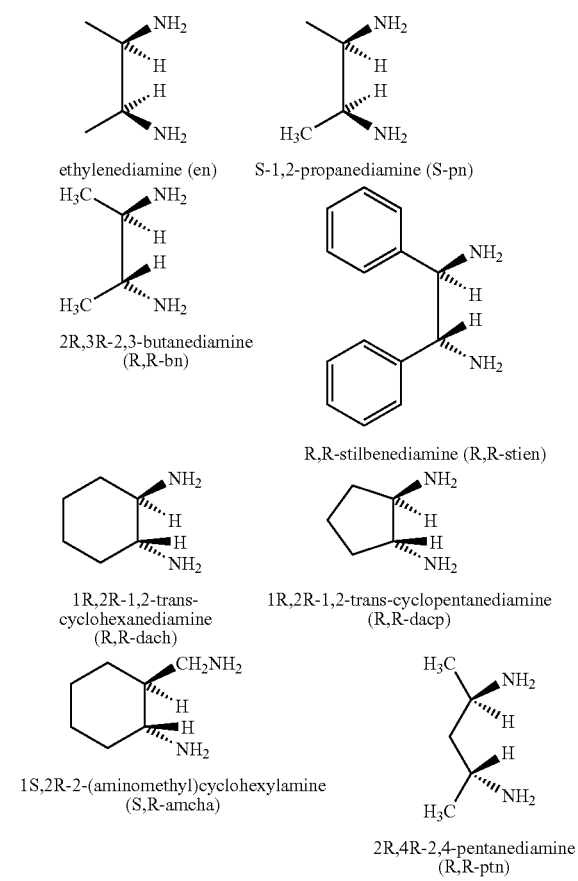

Suitable specific examples of the compound (II), which is one of the starting materials, include dinitrato(1R,2R-1,2-trans-cyclohexanediamine)platinum(II), dinitrato(1S,2S-1,2-trans-cyclohexanediamine)platinum(II), dichlorido(1R,2R-1,2-trans-cyclohexanediamine)platinum(II), dichlorido(1S,2S-1,2-trans-cyclohexanediamine)platinum(II), dinitrato(ethylenediamine)platinum(II), dinitrato(2R,3R-2,3-butanediamine)platinum(II), dinitrato(R,R-stilbenediamine)platinum(II), dinitrato(1S,2R-2-(aminomethyl)cyclohexylamine)platinum(II), and dinitrato(2R,4R-pentanediamine)platinum(II).

Specific examples of the compound (III), which is the other starting material, include L- or D-tartaric acid (abbreviation: L- or D-tartH$_4$), 1L,2L- or 1D,2D-2-methyltartaric acid (abbreviation: 1L,2L- or 1D,2D-mtartH$_4$), 2L,3L- or 2D,3D-2,3-dimethyltartaric acid (abbreviation: L- or D-dmtartH$_4$), 1L,2L- or 1D,2D-dihydroxycyclopentane-1,2-dicarboxylic acid (abbreviation: L- or D-cptartH$_4$), and 1L,2L- or 1D,2D-dihydroxycyclohexane-1,2-dicarboxylic acid (abbreviation: L- or D-chtartH$_4$). Structural formulae of the above compounds are shown below (the configuration of each compound shown below is not represented):

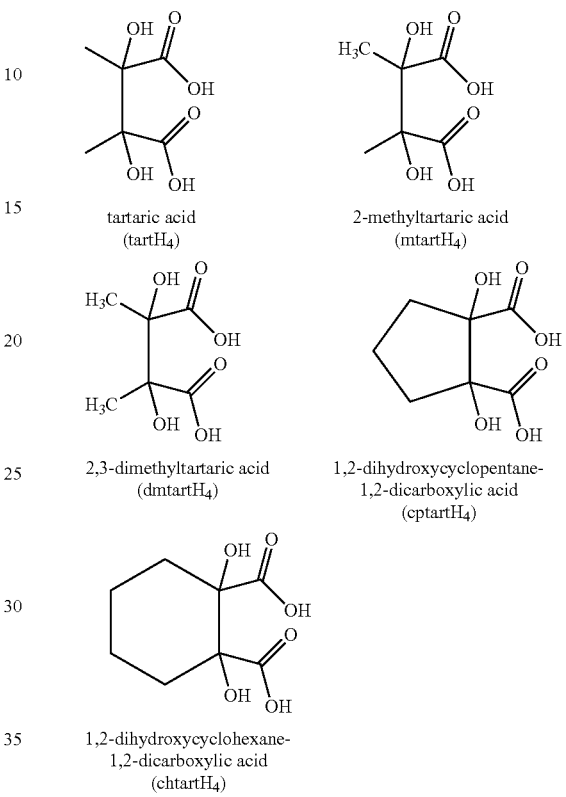

The above reaction is performed in an appropriate solvent. The solvent is preferably an aqueous solvent, and particularly preferably water.

Although the reaction temperature is not particularly limited, the above reaction is preferably performed at room temperature in general.

In this way, the optically active organic acidate-bridged dinuclear (diamine)platinum(II) complex represented as the compound (I) can be obtained in the form of a nitrate (X$^-$: NO$_3^-$), a chloride (X$^-$: Cl$^-$) or the like depending on the kind of the anion ligand group (X) of the starting material, i.e., the compound (II).

Another embodiment of the present invention is an optically active organic acidate-bridged dinuclear diammineplatinum(II) complex represented by the general formula (I'):

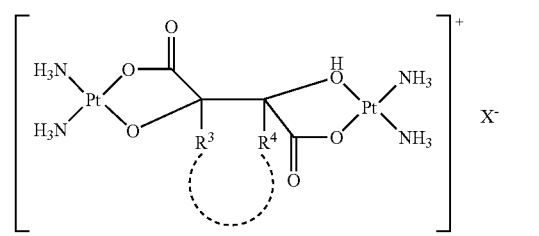

(wherein each symbol has the same meaning as above).

The above-mentioned complex can be prepared by reacting a compound represented by the general formula (II'):

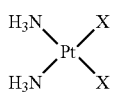
(II')

(wherein each symbol has the same meaning as above) with an optically active organic acid represented by the above-mentioned general formula (III). This reaction can be performed in the same manner as that of the above-mentioned compounds (II) and (III).

Specific examples of the compound (II') include cis-dichloridodiammineplatinum(II), cis-diiodidodiammineplatinum(II) and cis-dinitratodiammineplatinum(II).

The compounds (I) and (I') of the present invention both can be represented by the general formula (A):

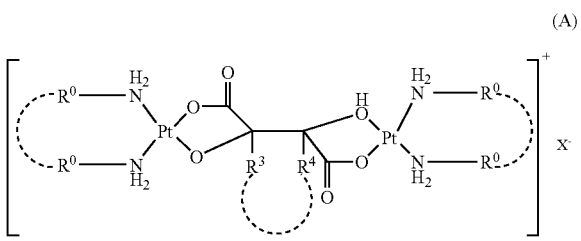
(A)

(wherein $R^0$ represents a hydrogen atom, or two neighboring $R^0$ bind to each other at the ends thereof to form a group represented by the following formula:

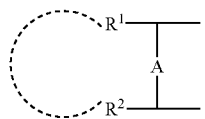

(wherein each symbol has the same meaning as above)).

Since the compounds (I) and (I') of the present invention have an excellent anticancer activity, they can be used as medicine. Namely, another embodiment of the present invention is an anticancer agent comprising, as an active ingredient, an optically active organic acidate-bridged dinuclear platinum(II) complex represented by the general formula (I) or (I').

The anticancer agent of the present invention can be administered orally or parenterally. The dosage form of the anticancer agent may be a liquid or solid preparation. Examples of the liquid preparation include solution for injection and suspension therefor. Examples of the solid preparation include capsules, tablets, powders and suppositories. If necessary, any of various organic or inorganic carrier substances that are conventionally used as a pharmaceutical material may be added to the anticancer agent in an appropriate amount as an excipient, a lubricant, a binder or a disintegrator in a solid preparation; or a solvent, a solubilizing agent, a suspending agent, an isotonizing agent, a buffering agent or a soothing agent in a liquid preparation. Suitable examples of the excipient include lactose, sucrose, D-mannitol, starch, crystalline cellulose and light silicic acid anhydride. Suitable examples of the lubricant include magnesium stearate, calcium stearate, talc and colloidal silica. Suitable examples of the binder include crystalline cellulose, sucrose, D-mannitol, dextrin, hydroxypropylcellulose, hydroxypropylmethylcellulose and polyvinylpyrrolidone. Suitable examples of the disintegrator include starch, carboxymethylcellulose, calcium carboxymethylcellulose, croscarmellose sodium and sodium carboxymethyl starch. Suitable examples of the solvent include water for injection. A conventional additive, such as solubilizing agents, suspending agents, isotonizing agents, buffering agents and preservatives may be added if needed.

The anticancer agent of the present invention can contain a dose determined according to a conventional pharmaceutical method. Although the dose of the anticancer agent varies with the kind and severity of disease, patient's body weight, the symptom, the administration route, etc., the daily dose is usually 0.1 to 100 mg/kg body weight, and preferably 1 to 30 mg/kg body weight in terms of the active ingredient. However, the dose of the anticancer agent of the present invention is not necessarily limited to the above range. Since the active ingredient of the anticancer agent of the present invention is superior in anticancer activity to oxaliplatin as clearly shown, for example, in the below-mentioned test examples, it can be expected to show an equivalent effect to oxaliplatin at a lower dose than that of oxaliplatin.

EXAMPLES

Hereinafter, the present invention will be illustrated in detail byway of examples and test examples, but is not limited thereto. The (dinitrato)1R,2R-1,2-trans-cyclohexanediamine platinum(II) ([Pt(NO$_3$)$_2$(R,R-dach)]) and (dinitrato)1S,2S-1,2-trans-cyclohexanediamine platinum(II) ([PT(NO$_3$)$_2$(S,S-dach)]) used as materials in the Examples were synthesized by known methods. The cis-dichloridodiammineplatinum(II) (cis-[PtCl$_2$(NH$_3$)$_2$]) used herein was a commercial product synthesized by a known method. In the Examples, the abbreviation "$(-)_D$" indicates that the optical rotation as measured at the sodium D-line (589 nm) is minus. $(-)_D$-2,3-dimethyltartaric acid with a specific rotation $[\alpha]_D$ of $-13.4°$ completely resolved is expressed as $(-)_D$-dmtartH$_4$ because it is unknown at present whether to be 2L,3L-2,3-dimethyltartaric acid, or 2D,3D-2,3-dimethyltartaric acid.

Example 1

To 5 ml of an aqueous solution containing 0.35 g (0.8 mmol) of (dinitrato)1R,2R-1,2-trans-cyclohexanediamine platinum(II) ([Pt(NO$_3$)$_2$(R,R-dach)]) was added 5 ml of an aqueous solution containing 0.06 g (0.4 mmol) of disodium L-tartrate dihydrate (Na$_2$L-tartH$_2$.2H$_2$O), and then stirring was performed at room temperature for 24 hours. Then, the reaction mixture was concentrated with an evaporator to give a yellow fine powder. After the powder was collected by filtration and redissolved in hot water, the resulting solution was filtered. The filtrate was reconcentrated to near dryness with an evaporator. The resulting powder was collected by filtration, washed with cold water and then alcohol, and dried to give about 230 mg of L-tartrate-bridged dinuclear 1R,2R-1,2-trans-cyclohexanediamine platinum(II) complex nitrate ([{Pt(R,R-dach)}$_2$(μ-L-tartH)]NO$_3$.4H$_2$O).
The Elementary Analysis Value of [{Pt(R,R-dach)}$_2$(μ-L-tartH)]NO$_3$.4H$_2$O:
    Calculated value (%): C, 21.34; H, 4.48; N, 7.78.
    Found value (%): C, 20.71; H, 4.24; N, 7.86.
$^1$HNMR and Infrared Absorption Spectra:
    The $^1$HNMR spectrum showed the coordination of tart and dach in a ratio of 1:2 in the complex.

A strong peak was observed at about 1600 cm$^{-1}$, and this result showed the coordination of tartrate in the complex.

Mass Spectrum: m/z

A peak was observed at 383 corresponding to the molecular mass of [{Pt(R,R-dach)}$_2$(μ--L-tartH$_2$)]$^{2+}$.

These results demonstrated the presence of a dinuclear structure in the resulting compound.

Example 2

Except that (dinitrato)1S,2S-1,2-trans-cyclohexanediamine platinum(II) ([Pt(NO$_3$)$_2$(S,S-dach)]) was used instead of (dinitrato)1R,2R-1,2-trans-cyclohexanediamine platinum (II) ([Pt(NO$_3$)$_2$(R,R-dach)]), the same procedure as described in Example 1 was performed to give L-tartrate-bridged dinuclear 1S,2S-1,2-trans-cyclohexanediamine platinum(II) complex nitrate ([{Pt(S,S-dach)}$_2$(μ-L-tartH)]NO$_3$.4H$_2$O).

The Elementary Analysis Value of [{Pt(S,S-dach)}$_2$(μ-L-tartH)]NO$_3$.4H$_2$O:

Calculated value (%): C, 21.34; H, 4.48; N, 7.78.
Found value (%): C, 21.48; H, 4.31; N, 7.34.

$^1$HNMR, Infrared Absorption and Mass Spectra:

Similar results were obtained to those in Example 1, and they demonstrated the coordination of tartrate and the presence of a dinuclear structure in the resulting compound.

Example 3

Except that disodium D-tartrate dihydrate (Na$_2$D-tartH$_2$.2H$_2$O) was used instead of disodium L-tartrate dihydrate, the same procedure as described in Example 1 was performed to give D-tartrate-bridged dinuclear 1R,2R-1,2-trans-cyclohexanediamine platinum(II) complex nitrate ([{Pt(R,R-dach)}$_2$(μ-D-tartH)]NO$_3$.4H$_2$O).

The Elementary Analysis Value of [{Pt(R,R-dach)}$_2$(μ-D-tartH)]NO$_3$.4H$_2$O:

Calculated value (%): C, 21.34; H, 4.48; N, 7.78. Found value (%): C, 21.36; H, 4.37; N, 7.78.

$^1$HNMR, Infrared Absorption and Mass Spectra:

Similar results were obtained to those in Example 1, and they demonstrated the coordination of tartrate and the presence of a dinuclear structure in the resulting compound.

Example 4

Except that disodium D-tartrate dihydrate was used instead of disodium L-tartrate dihydrate and that 1S,2S-cyclohexanediamine(dinitrato)platinum(II) ([Pt(NO$_3$)$_2$(S,S-dach)]) was used instead of (dinitrato)1R,2R-1,2-trans-cyclohexanediamine platinum(II) ([Pt(NO$_3$)$_2$(R,R-dach)]), the same procedure as described in Example 1 was performed to give D-tartrate-bridged dinuclear 1S,2S-cyclohexanediamine platinum(II) complex nitrate ([{Pt(S,S-dach)}$_2$(μ-D-tartH)]NO$_3$.4H$_2$O).

The Elementary Analysis Value of [{Pt(S,S-dach)}$_2$(μ-D-tartH)]NO$_3$.4H$_2$O:

Calculated value (%): C, 21.34; H, 4.48; N, 7.78.
Found value (%): C, 21.26; H, 4.30; N, 7.67.

$^1$HNMR, Infrared Absorption and Mass Spectra:

Similar results were obtained to those in Example 1, and they demonstrated the coordination of tartrate and the presence of a dinuclear structure in the resulting compound.

Example 5

Except that (−)$_D$-2,3-dimethyltartaric acid ((−)$_D$-dmtartH$_4$) and NaOH were used instead of disodium L-tartrate dihydrate, the same procedure as described in Example 1 was performed to give about 140 mg of (−)$_D$-2,3-dimethyltartrate-bridged dinuclear 1R,2R-1,2-trans-cyclohexanediamine platinum(II) complex nitrate ([{Pt(R,R-dach)}$_2$(μ-(−)$_D$-dmtartH)]NO$_3$.4H$_2$O).

The Elementary Analysis Value of [{Pt(R,R-dach)}$_2$((−)$_D$-dmtartH)]NO$_3$.4H$_2$O:

Calculated value (%): C, 23.30; H, 4.67; N, 7.55.
Found value (%): C, 22.80; H, 4.29; N, 7.47.

Infrared Absorption and $^1$HNMR Spectra:

A strong peak was observed at about 1600 cm$^{-1}$, and this result showed the coordination of tartrate in the complex. In the $^1$HNMR spectrum, signals from 26 protons of dmtart and R,R-dach were observed in the range of 1.06 to 2.31 ppm.

Mass Spectrum: m/z

792=[{Pt(R,R-dach)}$_2$((−)$_D$-dmtartH)]$^+$

The results demonstrated the presence of a dinuclear structure with bridging coordination of tartrate in the resulting compound.

Example 6

Except that (dinitrato)(1S,2S-1,2-trans-cyclohexanediamine)platinum complex was used instead of (dinitrato)(1R,2R-1,2-trans-cyclohexanediamine)platinum complex, the same procedure as described in Example 5 was performed to give (−)$_D$-2,3-dimethyltartrate-bridged dinuclear 1S,2S-1,2-trans-cyclohexanediamine platinum(II) complex nitrate ([{Pt(S,S-dach)}$_2$(μ-(−)$_D$-dmtartH)]NO$_3$.4H$_2$O).

The Elementary Analysis Value of [Pt$_2$(S,S-dach)$_2$((−)$_D$-dmtartH)]NO$_3$.4H$_2$O:

Calculated value (%): C, 23.30; H, 4.67; N, 7.55.
Found value (%): C, 22.72; H, 4.19; N, 7.38.

$^1$HNMR, Infrared Absorption and Mass Spectra:

Mass Spectrum: m/z

792=[Pt$_2$(S,S-dach)$_2$((−)$_D$-dmtartH)]$^+$

Similar results were obtained to those in Example 5, and they demonstrated the presence of a dinuclear structure with bridging coordination of tartrate in the resulting compound.

Example 7

150 mg of cis-[PtCl$_2$(NH$_3$)$_2$] was suspended in 5 ml of water. To this was added 170 mg of silver nitrate, and then stirring was performed at room temperature for 1 hour. After silver chloride was filtered off, 44.5 mg of (−)$_D$-dimethyltartaric acid ((−)$_D$-dmtartH$_4$) and 20 mg of sodium hydroxide were added to the filtrate, and then stirring was performed at room temperature for 12 hours. After the reaction mixture was filtered, the filtrate was concentrated with a rotary evaporator. Acetone was added to the concentrate to give a crude product. The crude product was recrystallized from water and acetone to give about 95 mg of (−)$_D$-2,3-dimethyltartrate-bridged dinuclear diammineplatinum(II) complex nitrate ([{Pt(NH$_3$)$_2$}$_2$((μ-(−)$_D$-dmtartH)]NO$_3$.6H$_2$O).

The Elementary Analysis Value of [{Pt(NH$_3$)$_2$}$_2$((−)$_D$-dmtartH)]NO$_3$.6H$_2$O:

Calculated value (%): C, 9.18; H, 3.72; N, 8.92.
Found value (%): C, 9.28; H, 3.51; N, 9.00.

Infrared Absorption and $^1$HNMR Spectra:

A strong peak was observed at about 1600 cm$^{-1}$, and this result showed the coordination of tartrate in the complex. In the $^1$HNMR spectrum, signals from 6 protons of the two methyl groups of dmtart were observed at 1.27 ppm.

Mass Spectrum: m/z

317=[{Pt(NH$_3$)$_2$}$_2$(dmtartH)+H]$^{2+}$

The above results were obtained, and they demonstrated the presence of a dinuclear structure with bridging coordination of dimethyltartrate in the resulting compound.

Example 8

Except that L-tartaric acid was used instead of $(-)_D$-2,3-dimethyltartaric acid ($(-)_D$-dmtartH$_4$), the same procedure as described in Example 7 was performed to give L-tartrate-bridged dinuclear diammineplatinum(II) complex nitrate ([{Pt(NH$_3$)$_2$}$_2$(μ-L-tartH)]NO$_3$.5H$_2$O).
The Elementary Analysis Value of [{Pt(NH$_3$)$_2$}$_2$(μ-L-tartH)]NO$_3$.5H$_2$O:
  Calculated value (%): C, 9.18; H, 3.72; N, 8.92.
  Found value (%): C, 9.28; H, 3.51; N, 9.00.
Infrared Absorption and $^1$HNMR Spectra:
A strong peak was observed at about 1600 cm$^{-1}$, and this result showed the coordination of tartrate in the complex. In the $^1$HNMR spectrum, signals from 2 protons of tart were observed at 4.82 ppm.
Mass Spectrum: m/z
  302=[{Pt(NH$_3$)$_2$}$_2$(L-tartH)+H]$^{2+}$
The above results were obtained, and they demonstrated the presence of a dinuclear structure with bridging coordination of tartrate in the resulting compound.

Test Example 1

The in vitro cancer growth inhibitory activity was assessed according to the method described in Jpn J Cancer Chemother, 24, 129 (1997) and Cancer Chemothr. Pharmacol., 52 Suppl 1, S74-79 (2003). Namely, a total of 39 different kinds of cancer cells at logarithmic growth phase were separately seeded into wells of 96 well plates, and incubated at 37° C. for 1 day. The cancer cells used were 5 kinds of breast cancer cells (HBC-4, BSY-1, HBC-5, MCF-7, MDA-MB-231), 6 kinds of glioma cancer cells (U251, SF-268, SF-295, SF-539, SNB-75, SNB-78), 5 kinds of colon cancer cells (HCC2998, KM-12, HT-29, HCT-15, HCT-116), 7 kinds of lung cancer cells (NCI-H23, NCL-H226, NCL-H522, NCL-H460, A549, DMS273, DMS114), 1 kind of melanoma cell (LOX-IMVI), 5 kinds of ovarian cancer cells (OVCAR-3, OVCAR-4, OVCAR-5, OVCAR-8, SK-OV-3), 2 kinds of renal cancer cells (RXF-631L, ACHN), 6 kinds of gastric cancer cells (St-4, MKN1, MKN7, MKN28, MKN45, MKN74), and 2 kinds of prostate cancer cells (DU-145, PC-3). Each sample solution was added to the wells on the following day, and culture was continued at 37° C. for another 2 days. Then, the degree of cell growth was determined by the colorimetric measurement using sulforhodamine B. The cancer growth inhibitory activity was assessed based on the average log GI$_{50}$ (GI$_{50}$ indicates the concentration required to inhibit 50% of cell growth) against 39 kinds of cancer cells. The results are shown in the following Table 1.

TABLE 1

| Compound | Cancer growth inhibitory activity (average log GI$_{50}$) |
|---|---|
| (Compound of the present invention) | |
| [{Pt(R,R-dach)}$_2$(μ-L-tartH)]NO$_3$•4H$_2$O | −5.99 |
| [{Pt(S,S-dach)}$_2$(μ-L-tartH)]NO$_3$•4H$_2$O | −5.36 |
| (Control compound) | |
| [Pt(L-HMB)(R,R-dach)]NO$_3$•4H$_2$O | −5.56 |
| [Pt(L-HMB)(S,S-dach)]NO$_3$•4H$_2$O | −4.95 |
| Oxaliplatin | −5.03 |

In the table, HMB represents 2-hydroxy-3-methyl-butanoic acid ion.

A comparison of the average log GI$_{50}$ was made between the compounds with a dinuclear structure of the present invention (tartrate complexes) and the control compounds with a mononuclear structure (2-hydroxy-3-methyl-butanoate complexes), specifically, between the R,R-dach isomers and between the S,S-dach isomers in the above table. In either case, the average log GI$_{50}$ of the compound of the present invention was improved by 0.4 or more than that of the counterpart. Since this difference exceeds 0.3, which is equivalent to log2, the compounds of the present invention are 2 or more times more excellent in the cancer growth inhibitory activity than the counterparts, and thus are shown to provide an effect of the dinuclear structure.

Test Example 2

The cancer growth inhibitory activity was assessed in the same manner as in Test Example 1, using colon cancer cell HT-29, lung cancer cell DMS273, gastric cancer cell MKN-7, and renal cancer cell RXF631L as cancer cells. The results are shown in the following Table 2.

TABLE 2

| | Cancer growth inhibitory activity (average log GI$_{50}$) | | | |
|---|---|---|---|---|
| Compound | colon cancer cell HT-29 | lung cancer cell DMS273 | gastric cancer cell MKN-7 | renal cancer cell RXF631L |
| (Compound of the present invention) | | | | |
| [{Pt(R,R-dach)}$_2$(μ-L-tartH)]NO$_3$•4H$_2$O | −7.00 | −7.31 | −4.98 | −4.92 |
| [{Pt(R,R-dach)}$_2$(μ-D-tartH)]NO$_3$•4H$_2$O | −5.96 | −7.46 | −6.02 | −6.03 |
| (Control compound) | | | | |
| Oxaliplatin | −4.91 | −6.06 | −4.68 | −4.13 |

As shown in the above table, [{Pt(R,R-dach)}$_2$(μ-L-tartH)]NO$_3$.4H$_2$O and [{Pt(R,R-dach)}$_2$(μ-D-tartH)]NO$_3$.4H$_2$O of the present invention exhibited about 20 times higher cancer growth inhibitory activity against lung cancer cells than oxaliplatin. [{Pt(R,R-dach)}$_2$(μ-L-tartH)]NO$_3$.4H$_2$O exhibited about 100 times stronger activity against colon cancer cells, and its mechanism of action can be considered unique in view of the correlation coefficient. [{Pt(R,R-dach)}$_2$(μ-D-tartH)]NO$_3$.4H$_2$O exhibited about 10 times (equivalent to 1 as a log value) stronger activity against colon cancer cells and gastric cancer cells and nearly 100 times stronger activity against renal cancer cells, and its mechanism of action is similar to that of oxaliplatin in view of the correlation coefficient. Further, the difference in anticancer activity between these diastereomers means that they have cell selectivity depending on optical isomerism (diastereomerism).

As for toxicity, most complexes of the present invention have a median lethal concentration ($LC_{50}$) of $10^{-4}$, which is equal to that of oxaliplatin and 2 digits higher than the $GI_{50}$ of the complexes. Compared to oxaliplatin, in which the difference is only 1 digit, the complexes of the present invention are effective from the viewpoint of toxicity as well.

INDUSTRIAL APPLICABILITY

The optically active organic acidate-bridged dinuclear platinum(II) complex of the present invention has an excellent anticancer activity, and is useful as medicine, especially an anticancer agent.

The invention claimed is:

1. An optically active organic acidate-bridged dinuclear (diamine)platinum(II) complex represented by the general formula (I):

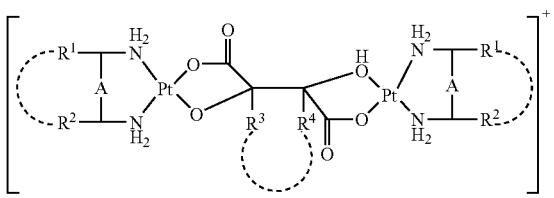

(I)

(wherein $R^1$ and $R^2$ are the same or different and each represent a hydrogen atom or an alkyl group, or form an alkylene group by binding to each other at the ends thereof;
$R^3$ and $R^4$ are the same or different and each represent a hydrogen atom or an alkyl group, or form an alkylene group by binding to each other at the ends thereof;
A represents a single bond or a methylene group; and
$X^-$ represents an anion).

2. The compound according to claim 1, wherein $R^1$ and $R^2$ form an alkylene group by binding to each other at the ends thereof and $R^3$ and $R^4$ are hydrogen atoms.

3. The compound according to claim 2, wherein the alkylene group which $R^1$ and $R^2$ form by binding to each other at the ends thereof is tetramethylene.

4. The compound according to claim 1, wherein A is a single bond.

5. The compound according to claim 1, wherein $X^-$ is a nitrate ion.

6. A method for preparing an optically active organic acidate-bridged dinuclear (diamine)platinum(II) complex represented by the general formula (I):

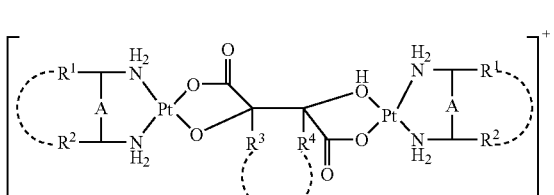

(I)

(wherein $R^1$ and $R^2$ are the same or different and each represent a hydrogen atom or an alkyl group, or form an alkylene group by binding to each other at the ends thereof;
$R^3$ and $R^4$ are the same or different and each represent a hydrogen atom or an alkyl group, or form an alkylene group by binding to each other at the ends thereof;
A represents a single bond or a methylene group; and
X represents an anion), which is characterized by reacting a platinum complex represented by the general formula (II):

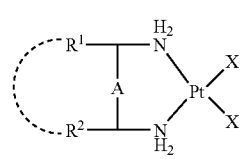

(II)

(wherein X represents an anion ligand, and the other symbols have the same meanings as above) with an optically active organic acid represented by the general formula (III):

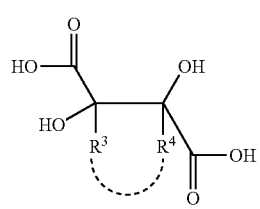

(III)

(wherein each symbol has the same meaning as above).

7. An anticancer agent comprising, as an active ingredient, an optically active organic acidate-bridged dinuclear (diamine)platinum(II) complex represented by the general formula (I):

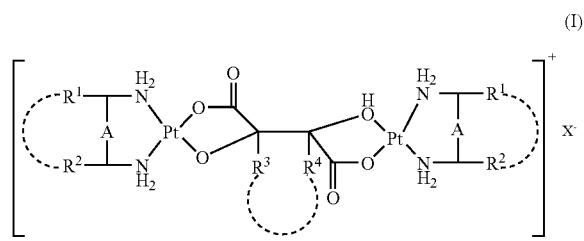

(I)

(wherein $R^1$ and $R^2$ are the same or different and each represent a hydrogen atom or an alkyl group, or form an alkylene group by binding to each other at the ends thereof;
$R^3$ and $R^4$ are the same or different and each represent a hydrogen atom or an alkyl group, or form an alkylene group by binding to each other at the ends thereof;
A represents a single bond or a methylene group; and
$X^-$ represents an anion).

8. An optically active organic acidate-bridged dinuclear diammineplatinum(II) complex represented by the general formula (I'):

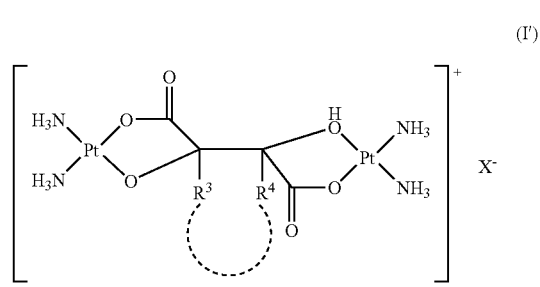

(I')

(wherein $R^3$ and $R^4$ are the same or different and each represent a hydrogen atom or an alkyl group, or form an alkylene group by binding to each other at the ends thereof; and $X^-$ represents an anion).

9. A method for preparing an optically active organic acidate-bridged dinuclear diammineplatinum(II) complex represented by the general formula (I'):

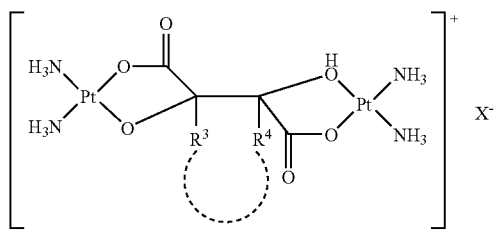
(I')

(wherein $R^3$ and $R^4$ are the same or different and each represent a hydrogen atom or an alkyl group, or form an alkylene group by binding to each other at the ends thereof; and $X^-$ represents an anion), which is characterized by reacting a platinum complex represented by the general formula (II'):

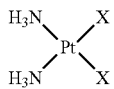
(II')

(wherein X represents an anion ligand)

with an optically active organic acid represented by the general formula (III):

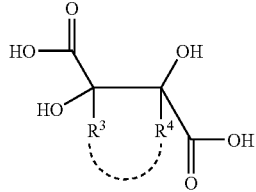
(III)

(wherein $R^3$ and $R^4$ have the same meanings as above).

10. An anticancer agent comprising, as an active ingredient, an optically active organic acidate-bridged dinuclear diammineplatinum(II) complex represented by the general formula (I'):

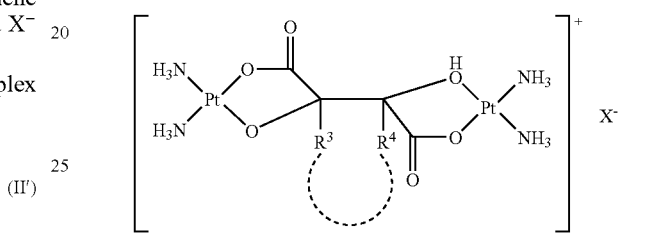
(I')

(wherein $R^3$ and $R^4$ are the same or different and each represent a hydrogen atom or an alkyl group, or form an alkylene group by binding to each other at the ends thereof; and $X^-$ represents an anion).

* * * * *